United States Patent [19]

Sudo et al.

[11] Patent Number: 5,009,646
[45] Date of Patent: Apr. 23, 1991

[54] SLIDING STOPPER FOR A SYRINGE

[75] Inventors: Masamichi Sudo; Tamotsu Okuda, both of Tokyo, Japan

[73] Assignee: Daikyo Gomu Seiko Ltd., Tokyo, Japan

[21] Appl. No.: 324,037

[22] Filed: Mar. 14, 1989

[30] Foreign Application Priority Data

Mar. 16, 1988 [JP] Japan .................. 63-33730

[51] Int. Cl.$^5$ .......................................... A61M 5/315
[52] U.S. Cl. ...................................................... 604/230
[58] Field of Search ............... 604/218, 220, 221, 222, 604/230

[56] References Cited

U.S. PATENT DOCUMENTS

| | | | |
|---|---|---|---|
| 2,578,394 | 12/1951 | Blackman | 604/221 |
| 2,607,342 | 8/1952 | Abel | 604/230 |
| 2,895,773 | 7/1959 | McConnaughey | 604/222 |
| 3,050,059 | 8/1962 | Wall et al. | 604/222 |
| 3,705,582 | 12/1972 | Stumpf et al. | 604/218 |
| 3,766,918 | 10/1973 | Kessel | 604/222 |
| 3,998,224 | 12/1976 | Chiquiar-Arias | 604/218 |
| 4,303,070 | 12/1981 | Ichikawa et al. | 604/222 |
| 4,501,192 | 2/1985 | Knödel | 604/230 |
| 4,685,910 | 8/1987 | Schweizer | 604/220 |
| 4,820,278 | 4/1989 | Balisky | 604/230 |

FOREIGN PATENT DOCUMENTS

| | | | |
|---|---|---|---|
| 0052889 | 4/1979 | Japan | 604/230 |
| 0551545 | 2/1943 | United Kingdom | 604/230 |
| 0702785 | 1/1954 | United Kingdom | 604/230 |

Primary Examiner—C. Fred Rosenbaum
Assistant Examiner—Sharon Rose
Attorney, Agent, or Firm—Wenderoth, Lind & Ponack

[57] ABSTRACT

A sliding stopper for a syringe, consisting of a rubber elastic body having the part to be contacted with a liquid medicament and the part sliding on the inner wall of a barrel fully laminated with a film of tetrafluoroethylene resin, ethylenetetrafluoroethylene resin or ultrahigh molecular weight polyethylene resin, and having an excellent liquid tightness and gas tightness. The ratio of the length (Y) of the surface of the outer circumferential part of the sliding stopper contacting the inner wall of the barrel to the length (L) of the sliding part of the sliding stopper, i.e. Y/L is in the range of 0.80 to 1.00, and the ratio of the length (L) of the sliding part to the outer diameter (D) of the sliding stopper, i.e. L/D is in the range of 0.25 to 1.00.

4 Claims, 2 Drawing Sheets

SLIDING STOPPER FOR A SYRINGE

BACKGROUND OF THE INVENTION

1. Field of the Invention

This invention relates to a sliding or movable stopper for an injector or syringe used for dosing a human body or animal with a liquid medicament.

2. Description of the Prior Art

An injector is generally constructed of a barrel 48 of a glass or thermoplastic plastic, a sliding stopper 41 of a glass, rubber or thermoplastic elastomer and a plunger rod 47, as shown in FIG. 5. A combination of a glass barrel and glass sliding stopper has rarely been used recently, but a combination of a glass barrel and elastomer sliding stopper has been used for a syringe additionally serving as a container to be filled with a liquid medicament and a combination of a plastic barrel and elastomer sliding stopper has ordinarily been used for a throwaway disposable syringe. FIG. 4 is a cross-sectional view of an elastomer sliding stopper 41 of the prior art, in which a sliding part on the inner wall of a barrel 48 has annular protrusions 45a and 45b which are contacted with the inner wall of the barrel.

Syringes or injectors must be germ-free and dust-free in view of their purpose and must have special physical properties such as liquid tightness, gas tightness and sliding property, which depend on the degree of contacting of the inner wall of a hard barrel with a sliding stopper consisting of an elastic material. Since every barrel has different straightness, smoothness and circular deformation of the inner wall and some errors in dimension and shape corresponding to the position, i.e. front part, central part and rear part, however, the above described degree of contacting in differs every barrel and every position of a barrel.

In order to correct such a differences, the diameter of a sliding stopper is ordinarily made larger than the average inner diameter of a barrel and the degree of contacting is increased to improve the liquid tightness and gas tightness. In this case, however, it is required to coat the sliding part with a silicone oil as a lubricant to make up for the thus lowered sliding property and the use of this silicone oil causes a problem of fine particle contamination of a medicament to be dosed.

To remedy this situation, the inventors have proposed a high quality syringe in which no silicone oil is required by laminating the surface of a sliding stopper with a fluoro resin and the contamination due to the silicone oil can thus be prevented, as disclosed in Japanese Patent Laid-Open Publication Nos. 243122/1986 and 139668/1987.

The laminated sliding stopper the inventors have proposed can completely solve the problem of contamination by a silicone oil as described above, but in a case where there are errors in dimension and shape of the inner wall of a barrel, the laminated sliding stopper cannot fully follow up the surface fluctuation as compared with non-laminated sliding stoppers, thus often resulting in deterioration of the sealability or tightness during sliding, i.e. using the syringe. Furthermore, the laminated sliding stopper often undergoes lowering of the tightness, in particular, in the case of twistdrawing when aspirating a liquid medicament or in the case of slant pushing when injecting a liquid medicament.

SUMMARY OF THE INVENTION

It is an object of the present invention to provide a sliding stopper for a syringe used for the injection of a liquid medicament, which will overcome the above described problems of the prior art.

It is another object of the present invention to provide a laminated sliding stopper with an improved sealability during sliding.

These objects can be attained by a sliding stopper for a syringe, consisting of a rubber elastic body whose part to be contacted with a liquid medicament and the part sliding on the inner wall of a barrel are fully laminated with a film of tetrafluoroethylene resin, ethylenetetrafluoroethylene resin or ultra-high molecular weight polyethylene resin, characterized in that the ratio of the length (Y) of the surface along which the outer circumferential part of the sliding stopper and the inner wall of the barrel are contacted to the length (L) of the sliding part of the sliding stopper, i.e. Y/L is in the range of 0.80 to 1.00, and the ratio of the length (L) of the sliding part to the outer diameter (D) of the sliding stopper, i.e. L/D is in the range of 0.25 to 1.00.

BRIEF DESCRIPTION OF THE DRAWINGS

The accompanying drawings are to illustrate in detail the principle and merits of the present invention.

DETAILED DESCRIPTION OF THE INVENTION

The inventors have made further studies to improve a laminated sliding stopper for a syringe, which consists of a rubber elastic body the part of which is to be contacted with an injection liquid and the part sliding on the inner wall of a barrel are fully laminated with a film of tetrafluoroethylene resin, ethylene-tetrafluoroethylene copolymer resin or ultra-high molecular weight polyethylene resin, and consequently have found that the sealability or tightness of the sliding stopper can be rendered sufficient to resist variation of the inner diameter or shape of the barrel and incorrect operation of the syringe by providing a specific relationship between the length (Y) of such a surface that the outer circumferential part of the sliding stopper and the inner wall of the barrel are contacted and the length (L) of the sliding part of the sliding stopper, and between the length (L) of the sliding part and the outer diameter (D) of the sliding stopper. That is, the ratio Y/L should be in the range of 0.80 to 1.00 and the ratio L/D should be in the range of 0.25 to 1.00. Preferably, L is in the range of 6 to 15 mm.

Figure 1:
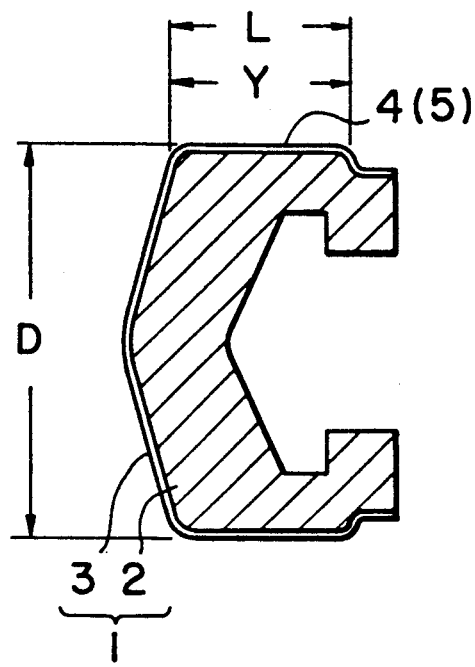
FIG. 1 and FIG. 2 are cross-sectional view of preferred embodiments of the sliding stopper for a syringe according to the present invention.
Figure 2:
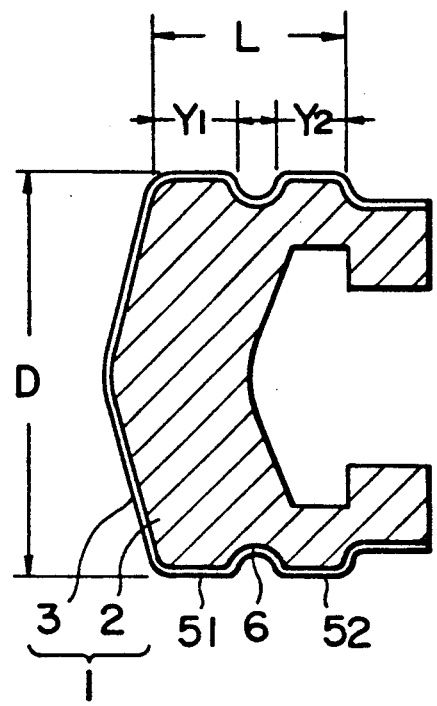
Figure 3:
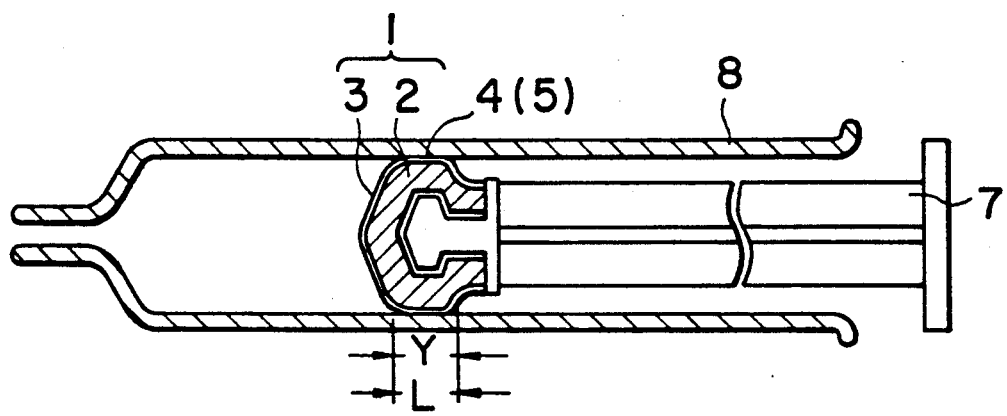
FIG. 3 is a cross-sectional view of another embodiment of the sliding stopper of the invention when applied to a syringe.

The present invention will now be illustrated in detail by the accompanying drawings. Referring to FIG. 1 and FIG. 2 showing cross-sectional views of preferred embodiments of the sliding stopper for a syringe according to the present invention and FIG. 3 showing a cross-sectional view of another embodiment of the sliding stopper of the present invention when applied to a syringe, a sliding stopper 1 consists of a rubber part 2 and a laminated resin film part 3 and is fitted to the end of a plunger rod 7 and inserted in a syringe barrel 8 as shown in FIG. 3. The feature of the present invention consists in that when the length of a sliding part 4 of the sliding stopper 1 is designated as L, the length of a part 5 of the sliding part 4, contacted with the inner wall of the syringe barrel 8, is designated as Y and the outer diameter of the sliding stopper is designated as D, Y is 80 to 100% of L, that is, Y/L is 0.80 to 1.00, and L is 25 to 100% of D, that is, L/D is 0.25 to 1.00. In the case of FIG. 1, the part 5 contacting the inner wall 8 of the syringe barrel 8 is an outer circumferential even surface of a cylinder and Y=L, i.e. Y is 100% of L, while as shown in FIG. 2, an annular hollow or recess part 6 can be provided between a contact part 51 (length $Y_1$) and another contact part 52 (length $Y_2$) in such a manner that the sum of $Y_1$ and $Y_2$ becomes 80 to 100% of L. Generally, the length L of the sliding part 4 is adjusted to about 6 to 15 mm, since the volume of an ordinary syringe corresponds to an injection liquid in an amount of 10 ml and this range of L can cover a liquid quantity of 3 to 25 ml.

Figure 4:
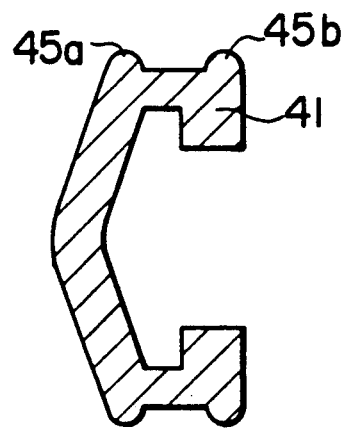
FIG. 4 and FIG. 5 are respectively cross-sectional views of a sliding stopper of the prior art and a syringe using this sliding stopper.
Figure 5:
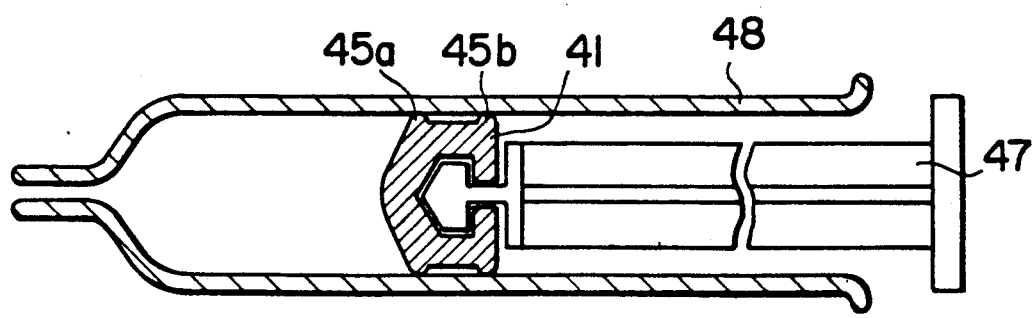

In the laminated sliding stopper of the prior art, annular protrusions 45a and 45b are provided at both the ends of the sliding part of a stopper 41, as shown in FIG. 4 (laminated film not shown), so as to maintain the sealability. In FIG. 5, 47 designates a plunger rod and 48, a barrel. In the present invention, on the contrary, the sealability can largely be improved by adjusting the overall surface of the sliding stopper, so that of the length Y of the contact surface with the inner wall of a barrel is substantiall 80 to 100% of the length of the sliding surface. Since the sliding surface has little or no unevenness, production of the sliding stopper by subjecting a rubber and resin film to molding and laminating can be accomplished without formation of scratches on convex parts and with a largely increased yield, thus lowering the production cost. Furthermore, the sealability can well be maintained even during incorrect operations such as twist drawing and slant pushing by adjusting L to 25 to 100% of D.

The factor having the largest influence upon the sliding property is the friction resistance of the surface of a sliding stopper. Thus, a fluoro resin film having a small friction coefficient such as tetrafluoroethylene resin films (hereinafter referred to as TFE) or ethylenetetrafluoroethylene resin films (hereinafter referred to as ETFE) is preferably used as the laminated layer 3 on the surface of the sliding stopper according to the present invention. In addition, polyethylene resins (referred to as PE) having an ultra-high molecular weight, i.e. at least $100 \times 10^4$, which have lately been developed, are also preferably used as the material of the laminated layer, because of having a similar friction coefficient to fluororesins, being sufficiently resistant during practical use and also resistant to a gamma-ray sterilization method which has lately been used often and being able to produced at a low cost. The laminated layer preferably has a thickness of 0.010 to 0.2 mm.

Production of the sliding stopper according to the present invention can be carried out by placing a film for lamination on the surface of a rubber sheet and then simultaneously subjecting the film and sheet to molding and laminating. For such rubber sheet, for example, natural rubber and synthetic rubbers can be used.

The sliding stopper of the present invention has the following advantages:

In the sliding stopper of the present invention, the surface of an elastic rubber body is laminated with a resin film with an excellent chemical resistance, but the sealability or tightness of the sliding stopper can be made sufficient to accommodate variation of the inner diameter or shape of a syringe barrel and incorrect operation of the syringe during use by a specific relationship between the length of such a surface and the length of the outer circumferential part of the sliding stopper that contacts the inner wall of the barrel, and the relationship between the length of the sliding part of the sliding stopper and the outer diameter of the sliding stopper. Furthermore, the use of silicone oil is not required and contamination of a liquid medicament with fine particles due to such use can be prevented. Therefore, the sliding stopper of the present invention can be favorably applied to a syringe or injector for dosing a high purity medicament with in high security as well as a syringe additionally serving as a container for a liquid medicament, because of its high chemical resistance and sealability.

The following examples are given in order to illustrate the present invention in greater detail without limiting the same.

EXAMPLES

Sliding stoppers of the present invention, each having a shape as shown in FIG. 1 or FIG. 2 and a laminated layer consisting of TFE, ETFE or PE, were prepared while varying Y/L and L/D within the scope of the present invention (Examples 1 to 6).

On the other hand, stoppers having no laminated layer as shown in FIG. 4 (Comparative Examples 1 to 3, commercially available) and a laminated stopper (Comparative Example 4) were prepared.

These samples were subjected to an elution or extraction test according to a legal test method, as a physical property test of the sliding stopper itself, and to the legal physical test and the physical test and fine particle test according to an independent test standard to evaluate the properties when used for a syringe. The outlines of these test methods are illustrated below and the test results are shown in the following table with the standard values:

LEGAL TEST (1) According to the test methods described in Notification No. 442 of the Welfare Ministry, Standard for Syringe Barrel of Disposal type, extraction tests with water (A) or a solvent (B) and physical tests (C) including a pressure test, aspiration test and movement test were carried out.

(2) According to 44 Test Method of Rubber Stopper for Liquid Transfusion of 11th Revision, Japanese Pharmacopoeia, an extraction test (D) was carried.

INDEPENDENT TEST METHOD

Twist Drawing Test:

Leakage of air was examined when 2 ml of water was charged in a syringe barrel, a needle opening part was directed upward and clogged and a plunger rod was withdrawn by fingers while revolving it by about 90 degrees.

Slant Pushing Test:

Leakage of water was examined when 2 ml of water was charged in a syringe barrel, a plunger rod was positioned in such a manner that the sliding stopper was at the maximum scale mark, a needle opening was directed upward and clogged and the plunger rod was pushed while in a slant state.

Sliding Test:

A syringe barrel to which an injection needle was not attached was fixed and a plunger rod was thrust to move the sliding stopper, and the load (initial value and sliding value) was measured by an Autograph DCS-100 type (commerical name, manufactured by Shimazu Seisakusho KK).

Knocking Test (Fluctuation of Sliding Value):

"Good" means a state in which when a plunger rod is thrust in a syringe barrel by hand, it is moved in smooth and continuous manner, while "knocking" means a state in which the plunger rod is intermittently moved. The knocking property is an important property to judge whether an injection medicament is precisely dosed as predetermined or not.

Deairing Test:

After purified water was aspirated in a syringe to the maximum scale mark and then 1 ml was discharged by thrusting a plunger rod with a needle directed upward, the presence or absence of bubbles was visually examined. Mark shows a bubble-free state and mark x shows a bubbled state.

Fine Particle Test:

This test was carried out by aspirating 5 ml of purified water by a syringe, discharging the water by thrusting the plunger and collecting the discharge water, repeating this procedure three times to obtain a test liquid and after allowing the discharge water to stand for 30 minutes, subjecting 12 ml of the test liquid to measurement using an optical fine particle tester (RION). In each Example, 20 samples were used and subjected to this test and the results are shown in the following table as mean values per one sample.

The assessment of the results is represented by "Very Good" ⊚, "Good" O, "Normal" Δ and "Unsuitable" x.

"ND" means an amount lower than the limit which can be detected.

TABLE

|  |  |  | Examples | | | | | |
| --- | --- | --- | --- | --- | --- | --- | --- | --- |
|  |  | No. | 1 | 2 | 3 | 4 | 5 | 6 |
|  |  | Y/L (%) | 100 | 100 | 100 | 85 | 85 | 80 |
|  |  | L/D (%) | 100 | 50 | 25 | 100 | 70 | 25 |
|  | Laminated Layer Resin |  | PE | PTFF | PTFE | PE | ETFE | PE |
| Legal Test | Standard for Syringe Barrel | (A) Appearance |  |  |  |  |  |  |
|  |  | pH | +0.03 | +0.04 | +0.03 | +0.05 | +0.03 | +0.05 |
|  |  | Heavy Metals (mg) | ND | ND | ND | ND | ND | ND |
|  |  | KMnO$_4$ Reducing Materials (mg) | 0.1 | 0.12 | 0.09 | 0.08 | 0.11 | 0.12 |
|  |  | Evaporation Residues (mg) | ND | ND | ND | ND | ND | ND |
|  |  | (B) Extraction Trifluoro-trichlorethane (Silicone Oil) (mg) | ND | ND | ND | ND | ND | ND |
|  |  | (C) Pressure Test | suitable | suitable | suitable | suitable | suitable | suitable |
|  |  | Aspiration Test | suitable | suitable | suitable | suitable | suitable | suitable |
|  |  | Movement Test | suitable | suitable | suitable | suitable | suitable | suitable |
|  | pharmacopoeia | (D) Percent Transmission of Visible Rays 430 Nm | 99.9 | 99.9 | 99.9 | 99.9 | 99.9 | 99.9 |
|  |  | 650 Nm | 100 | 100 | 100 | 100 | 100 | 100 |
|  |  | UV Absorption Spectrum 220-350 Nm | 0.015 | 0.023 | 0.028 | 0.018 | 0.032 | 0.023 |
|  |  | KMnO$_4$ Reducing Materials (ml) | 0.43 | 0.36 | 0.25 | 0.33 | 0.38 | 0.40 |
| Independent Test | Physical Test | Twist Drawing Test | no | no | no | no | no | no |
|  |  | Slant Pushing Test | no | no | no | no | no | no |
|  |  | Sliding Test (initial value g) | 420 | 380 | 400 | 460 | 370 | 460 |
|  |  | Sliding Test (sliding value g) | 310 | 230 | 230 | 240 | 190 | 250 |
|  |  | Knocking Property | good | good | good | good | good | good |
|  |  | Deairing Property |  |  |  |  |  |  |
|  | Fine Particle Test | Fine Particles |  |  |  |  |  |  |
|  |  | 2μ or more | 250 | 280 | 310 | 290 | 270 | 320 |
|  |  | 5μ or more | 40 | 43 | 56 | 40 | 39 | 51 |
|  |  | 10μ or more | 0 | 0 | 1 | 0 | 0 | 1 |
|  |  | 20μ or more | 0 | 0 | 0 | 0 | 0 | 0 |
|  |  | 30μ or more | 0 | 0 | 0 | 0 | 0 | 0 |
| Asessment |  | Extraction Test and Fine Particle Test Physical Test General Assessment |  |  |  |  |  |  |

|  |  |  | Comparative Examples | | | | |
| --- | --- | --- | --- | --- | --- | --- | --- |
|  |  | No. | 1 | 2 | 3 | 4 |  |
|  |  | Y/L (%) | 30 | 25 | 27 | 30 |  |
|  |  | L/D (%) | 45 | 56 | 55 | 51 | standard |
|  | Laminated Layer Resin |  | no | no | no | ETFE |  |
| Legal Test | Standard for Syringe Barrel | (A) Appearance | Δ | Δ | Δ |  | colorless, clear, no foreign matters |
|  |  | pH | +0.35 | +0.4 | +0.3 | +0.05 | at most 2.0 |
|  |  | Heavy Metals (mg) | ND | ND | ND | ND | at most 2 |
|  |  | KMnO$_4$ Reducing Materials (mg) | 0.31 | 0.42 | 0.36 | 0.12 | at most 2 |
|  |  | Evaporation | 3.2 | 2.8 | 3.0 | 0.01 | at most 1 |

TABLE-continued

| | | | | | | | |
|---|---|---|---|---|---|---|---|
| | | Residues (mg) (B) Extraction Trifluorotrichloroethane (Silicone Oil) (mg) | 5.9 | 6.3 | 7.3 | ND | at most 5 |
| | | (C) Pressure Test | suitable | suitable | suitable | suitable | |
| | | Aspiration Test | suitable | suitable | suitable | suitable | |
| | | Movement Test | suitable | suitable | suitable | suitable | |
| | pharmacopoeia | (D) Percent Transmission of Visible Rays 430 Nm | 80.3 | 84.3 | 85.3 | 98.0 | at least 98.0 |
| | | 650 Nm | 89.5 | 92.1 | 91.2 | 99.0 | |
| | | UV Absorption Spectrum 220–350 Nm | 1.80 | 1.25 | 1.32 | 0.04 | at most 0.2 |
| | | $KMnO_4$ Reducing Materials (ml) | 26.3 | 18.3 | 6.3 | 0.82 | at most 0.2 |
| Independent Test | Physical Test | Twist Drawing Test | small | small | no | small | |
| | | Slant Pushing Test | small | small | small | small | |
| | | Sliding Test (initial value g) | 320 | 420 | 530 | 830 | |
| | | Sliding Test (sliding value g) | 200 | 250 | 350 | 520 | |
| | | Knocking Property | some knocking | knocking | some knocking | good | |
| | Fine Particle Test | Deairing Property Fine Particles | X | X | X | | |
| | | $2\mu$ or more | 6210 | 5030 | 1300 | 420 | |
| | | $5\mu$ or more | 130 | 120 | 230 | 70 | |
| | | $10\mu$ or more | 27 | 42 | 52 | 15 | |
| | | $20\mu$ or more | 58 | 8 | 10 | 3 | |
| | | $30\mu$ or more | 10 | 1 | 0 | 0 | |
| Asessment | | Extraction Test and Fine Particle Test | X | X | X | | |
| | | Physical Test | Δ | Δ | Δ | | |
| | | General Assessment | Δ | Δ | Δ | | |

As can be seen from these results, the commercially available sliding stoppers with no lamination layer as shown in FIG. 4 (Comparative Examples 1 to 3) all give good results in the physical tests, but inferior results in the fine particle test which will cause a problem with safety considering a bad influence on a human body whereas the sliding stopper having a laminated layer and a shape as shown in FIG. 4 (Comparative Example 4) exhibits a very high safety, but meets with a problem in the physical tests. On the other hand, all the samples of the present invention give much better results in all the tests, which can favorably be compared with those of the Comparative Examples, and achieve fully the objects of the present invention.

What is claimed is:

1. A sliding stopper for a syringe, consisting of a rubber elastic body having a part to be contacted with a liquid medicament and a part slidable on the inner wall of a barrel fully laminated with a resin film having a small friction coefficient, the ratio of the length (Y) of the surface of the outer circumferential part of the sliding stopper contacting the inner wall of the barrel to the length (L) of the slidable part of the sliding stopper, Y/L being in the range of 0.8 to 1, and the ratio of the length (L) of the slidable part of the outer diameter (D) of the sliding stopper L/D being in the range of 0.25 to 1.

2. The sliding stopper for a syringe, as claimed in claim 1, wherein the resin film is selected from the group consisting of films of tetrafluoroethylene resin, ethylenetetrafluoroethylene copolymer resins and ultrahigh molecular weight polyethylene resin.

3. The sliding stopper for a syringe, as claimed in claim 1, wherein the length (L) of the sliding part is from 6 mm to 15 mm.

4. The sliding stopper for a syringe, as claimed in claim 1, wherein the part of the sliding stopper contacting the inner wall of the barrel, having the length (Y), is provided with an annular recess dividing the length Y into two parts respectively having lengths $Y_1$ and $Y_2$ and $(Y_1+Y_2)/L$ is in the range of 0.8 to 1.

* * * * *